(12) United States Patent
Strauss et al.

(10) Patent No.: US 10,793,852 B2
(45) Date of Patent: Oct. 6, 2020

(54) HIGH-DENSITY DNA STORAGE WITH SALT

(71) Applicant: MICROSOFT TECHNOLOGY LICENSING, LLC, Redmond, WA (US)

(72) Inventors: Karin Strauss, Seattle, WA (US); Weida Chen, Zürich (CH); Robert Grass, Zürich (CH); Alexander Xavier Christof Kohll, Zürich (CH); Bichlien Hoang Nguyen, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 16/017,714

(22) Filed: Jun. 25, 2018

(65) Prior Publication Data

US 2019/0390194 A1     Dec. 26, 2019

(51) Int. Cl.
| | |
|---|---|
| *C07H 21/00* | (2006.01) |
| *C12N 15/11* | (2006.01) |
| *G06N 3/12* | (2006.01) |
| *C07H 21/02* | (2006.01) |
| *C07H 21/04* | (2006.01) |

(52) U.S. Cl.
CPC ............. *C12N 15/11* (2013.01); *G06N 3/123* (2013.01); *C07H 21/00* (2013.01); *C07H 21/02* (2013.01); *C07H 21/04* (2013.01)

(58) Field of Classification Search
None
See application file for complete search history.

(56) References Cited

U.S. PATENT DOCUMENTS

| | | | | |
|---|---|---|---|---|
| 2006/0094015 A1* | 5/2006 | Smith | ................ | C12N 15/1006 435/6.11 |
| 2017/0151545 A1 | 6/2017 | Horton et al. | | |

OTHER PUBLICATIONS

Lahiri et al. Biochemical Genetics (1993), vol. 31, pp. 321-328.*
Lee et al. Nucleic Acids Research (1997), vol. 25, pp. 2816-2822.*
Grass, et al., "Robust Chemical Preservation of Digital Information on DNA in Silica with Error-Correcting Codes", In Publication of Angewandte Chemie International Edition, Feb. 16, 2005, pp. 2552-2555.
Paunescu, et al., "Reversible DNA encapsulation in silica to produce ROS-resistant and heat resistant synthetic DNA 'fossils'", In Journal of Nature Protocol, vol. 8, Issue 12, Dec. 2013, pp. 2440-2448.
Anchordoquy, et al., "Preservation of DNA", Published in Journal of Cell Preservation Technology, vol. 5, Issue 4, Dec. 1, 2007, pp. 180-188.
Ausubel, et al., "Current Protocols in Molecular Biology", In Publication of John Wiley & Sons, Inc, Jan. 1, 1996, 13 Pages.

"International Search Report and Written Opinion Issued in PCT Application No. PCT/US19/036215", dated Sep. 23, 2019, 11 Pages.
Lee, et al., "Assessing a Novel Room Temperature DNA Storage Medium for Forensic Biological Samples", Published in Journal of Forensic Science International: Genetics, vol. 6, issue 1, Jan. 1, 2012, 10 Pages.
Kuroda, et al., "Simplified Lentivirus Vector Production in Protein-Free Media using Polyethylenimine-Mediated Transfection", In Journal of Virological Methods vol. 157, Issue 2, May 2009, pp. 113-121.
Turon, et al., "Surviving Mass Extinctions through Biomineralized DNA", Published in Chemistry—A European Journal vol. 21, Issue 52, Dec. 21, 2015, 8 Pages.
Bonnet, et al., "Chain and Conformation Stability of Solid-State DNA: Implications for Room Temperature Storage", In Journal of Nucleic Acids Research, vol. 38, Issue 5, Dec. 7, 2009, pp. 1531-1546.
Yang, et al., "The Effect of Amorphous Calcium Phosphate on Protein Protection Against Thermal Denaturation", In Journal of Chemical Communications, vol. 51, Issue 41, Apr. 20, 2015, pp. 8705-8707.
Celina, et al., "Accelerated Aging and Lifetime Prediction: Review of Non-Arrhenius Behaviour Due to Two Competing Processes", In Journal of Polymer Degradation and Stability, vol. 90, Issue 3, Jul. 5, 2005, pp. 395-404.
Organick, et al., "Random Access in Large-Scale DNA Data Storage", In Journal of Nature Biotechnology, vol. 36, Issue 3, Feb. 19, 2018, 9 Pages.
Valle, et al., "DNA Adsorbed on Hydroxyapatite Surfaces", In Journal of Materials Chemistry B, vol. 2, Issue 40, Aug. 15, 2014, pp. 6953-6966.
Pedraza, et al., "The Importance of Particle Size and DNA Condensation Salt for Calcium Phosphate Nanoparticle Transfection", In Journal of Biomaterials, vol. 29, Issue 23, Aug. 2008, pp. 3384-3392.
Church, et al., "Next-Generation Digital Information Storage in DNA", In Journal of Science, vol. 337, Issue 5102, Sep. 28, 2012, 2 Pages.
Clermont, et al."Assessment of DNA Encapsulation, a New Room-Temperature DNA Storage Method", In Journal of Biopreservation and Biobanking, vol. 12, Issue 3, Jun. 1, 2014, pp. 176-183.
Dabney, et al., "Complete Mitochondrial Genome Sequence of a Middle Pleistocene Cave Bear Reconstructed from Ultrashort DNA Fragments", In Proceedings of the National Academy of Sciences, vol. 110, Issue 39, Sep. 24, 2013, pp. 15758-15763.

(Continued)

*Primary Examiner* — Patrick T Lewis
(74) *Attorney, Agent, or Firm* — Newport IP, LLC; Benjamin A. Keim

(57) ABSTRACT

A data storage medium is disclosed comprising a dried product formed by drying a salt solution dried together with artificially synthesized DNA molecules encoding digital information. The cation in the salt may be calcium, magnesium, lanthanum, or another cation. The anion in the salt may be chloride, phosphate, or another anion. The DNA is protected from degradation by drying with the salt. Stored DNA may be freed from the salt for sequencing or other analysis by mixing the dried product with a chelator. The dry product formed from DNA and a salt may contain more than 30% DNA by weight and degrade at rates that are less than a third of rate at which untreated DNA degrades.

20 Claims, 3 Drawing Sheets

(56) References Cited

OTHER PUBLICATIONS

Erlich, et al., "DNA Fountain Enables a Robust and Efficient Storage Architecture", In Journal of Science, vol. 355, Issue 6328, Mar. 3, 2017, 53 Pages.
Goldman, et al.,"Towards Practical, High-capacity, Low-maintenance Information Storage in Synthesized DNA", In Journal of Nature, vol. 494, Issue 7435, Jan. 23, 2013, pp. 77-80.
Graham, et al., "A New Technique for the Assay of Infectivity of Human Adenovirus 5 DNA", In Journal of Virology, vol. 52, Issue 2, Apr. 1973, pp. 456-467.
Serec, et al., "Effect of Magnesium Ions on the Structure of DNA Thin Films: An Infrared Spectroscopy Study", In Journal of Nucleic Acids Research, vol. 44, Issue 17, Aug. 2, 2016, pp. 8456-8464.
Reinsel, et al., "Data Age 2025: The Evolution of Data to Life-Critical: Don't Focus on Big Data; Focus on the Data That's Big", In IDC White Paper, Apr. 2017, 25 Pages.
Li, et al., "Self-assembled CaP-based Hybrid Nanoparticles to Enhance Gene Transfection Efficiency in Vitro and in Vivo: Beneficial Utilization of Pegylated Bisphosphate and Nucleus Locating Signal", In Journal of Materials Chemistry 3, vol. 6, Issue 21, Apr. 30, 2018, pp. 3466-3474.
Lindahl, et al., "Rate of Depurination of Native Deoxyribonucleic Acid", In Journal of Biochemistry, vol. 11, Issue 19, Sep. 12, 1972, pp. 3610-3618.
Liu, et al., "Template-Assisted Self-Assembly: Alignment, Placement, and Arrangement of Two-Dimensional Mesostructured DNA—Silica Platelets", In Journal of Angewandte Chemie International Edition, vol. 52, Issue 52 Dec. 23, 2013, pp. 14186-14190.
Marguet, et al., "DNA Stability at Temperatures Typical for Hyperthermophiles", In Journal of Nucleic Acids Research, vol. 22, Issue 9, May 11, 1994, pp. 1681-1686.
Marguet, et al., "Protection of DNA by Salts against Thermodegradation at Temperatures Typical for Hyperthermophiles", In Journal of Extremophiles, vol. 2, Issue 2, May 1998, pp. 115-122.
Murai, et al., "Efficient Catalytic Addition of Aromatic Carbon-Hydrogen Bonds to Olefins", In Journal of Nature, vol. 366, Issue 6455, Dec. 9, 1993, pp. 529-531.

\* cited by examiner

HIGH-DENSITY DNA STORAGE WITH SALT

BACKGROUND

The volume of digital information is increasing at an exponential rate. This vast increase in the amount of digital information may outpace the ability of conventional storage technologies. One promising technology for storing large amounts of digital information is deoxyribonucleic acid (DNA). DNA is well known as a molecule that can store genetic information. However, DNA can also function as a storage medium for digital information. Multiple different groups have successfully converted computer files into a string of nucleotide bases, created synthetic DNA encoding that string, sequenced the synthetic DNA, and then recovered the original digital information with 100% accuracy.

As a storage medium, DNA has potential advantages over conventional optical and magnetic media in terms of information densities and stability. Storage using DNA can achieve data density of over 200 petabytes (i.e., 200 million gigabytes) per gram which is much higher than possible with conventional media. With DNA it is possible that all the digital information in the world could be stored in a single room. DNA can also provide better long-term storage. Magnetic and optical media can wear out within 5 to 10 years. However, readable DNA has been recovered from fossils hundreds of thousands of years old.

Longevity of DNA, however, depends on storage conditions. DNA is susceptible to degradation by heat, enzymes, mutagenic chemicals, and ionizing radiation. When stored in solution DNA is stable for approximately 10 years, which is the same timescale as other storage media. Storage techniques that provide long-term stability and high data density improve the usability of DNA as a storage medium for digital information.

SUMMARY

This disclosure provides structures and methods for long-term, high-density storage of DNA through drying in the presence of a salt. The DNA is associated with a salt as a salt solution dries. DNA stored in this manner is more stable than unprotected DNA. This storage technique also achieves greater DNA densities than other long-term DNA storage technologies. The structures and techniques described in this disclosure provide for stable DNA storage such that less than half of the DNA degrades during one day of storage at 70° C. and 50% relative humidity (RT). Storing DNA at this elevated temperature is a way to roughly represent 2000 years of storage at room temperature. The salts may also be loaded with greater than 10% DNA by weight which compares favorably with other protocols that achieve roughly 0.2-0.7 wt % DNA in the final product. See Paunescu et al., *Reversible DNA Encapsulation in Silica to Produce ROS-resistant and Heat-resistant Synthetic DNA 'Fossils'*, 8:12 Nature Protocols 2440 (2013).

The salts may include salts with any of various cations and anions such as calcium phosphate, magnesium chloride, and others. For example, cations in the salts may be one or more of calcium, magnesium, and lanthanum. Anions in the salts may be chloride, fluoride, nitride, bromide, iodide, phosphate, carbonate, nitrate, perchlorate, iodate, bromate, or others. Without being bound by theory, it is believed that as a solution of salt ions and DNA dries, the DNA molecules are present within the crystal structure of the salt and stabilized. The solution may be dried by evaporation with a vacuum centrifuge or other technique. The ratio of DNA to salt in solution achieves a balance between stability and storage density. Too little salt and the DNA will have stability characteristics similar to untreated DNA. Too much salt, and the stored material will be mostly salt. Surprisingly, compositions that contain as much as 30-50 wt % DNA exhibit marked increases in stability as compared to untreated DNA. The levels of stability achieved by adding relatively small amounts of salt were not expected.

These structures and techniques described in this disclosure have applications for storing synthetic DNA encoding digital information but are equally suitable for storing other types of DNA such as naturally occurring DNA.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Polynucleotides such as DNA and ribonucleic acid (RNA) may be used to store digital information by designing a sequence of nucleotide bases that encodes the zeros and ones of the digital information. There are various techniques and encoding schemes known to those of skill in the art for using nucleotide bases to represent digital information. See Grass et al., *Robust Chemical Preservation of Digital Information on DNA in Silica with Error-correcting Codes*, 54 Angew. Chem. Int. Ed. 2552 (2015). Advantages of using DNA rather than another storage media for storing digital information include information density and longevity. The DNA storage structure and methods described in this disclosure can improve both information density and longevity relative to other techniques for storing DNA. The contents of the disclosure may be used with any type of polynucleotide, thus references to "DNA" are illustrative and not intended to limit the application to a particular type of polynucleotide.

The term "stably storing" refers to storage conditions that preserve the items stored in an unchanged or substantially unchanged condition for a period of time longer than the item would be unchanged absent the specific storage conditions. In the context of DNA storage, "stably storing" may refer to storing DNA at room temperature and relative humidity of approximate 50% for greater than 10 years with less than 1% degradation. "Stably storing" may also refer to a technique or structure for storage the reduces degradation of the items stored to a rate that is less than half that of items stored under similar conditions without use of the specific storage technique or structure.

Figure 1:
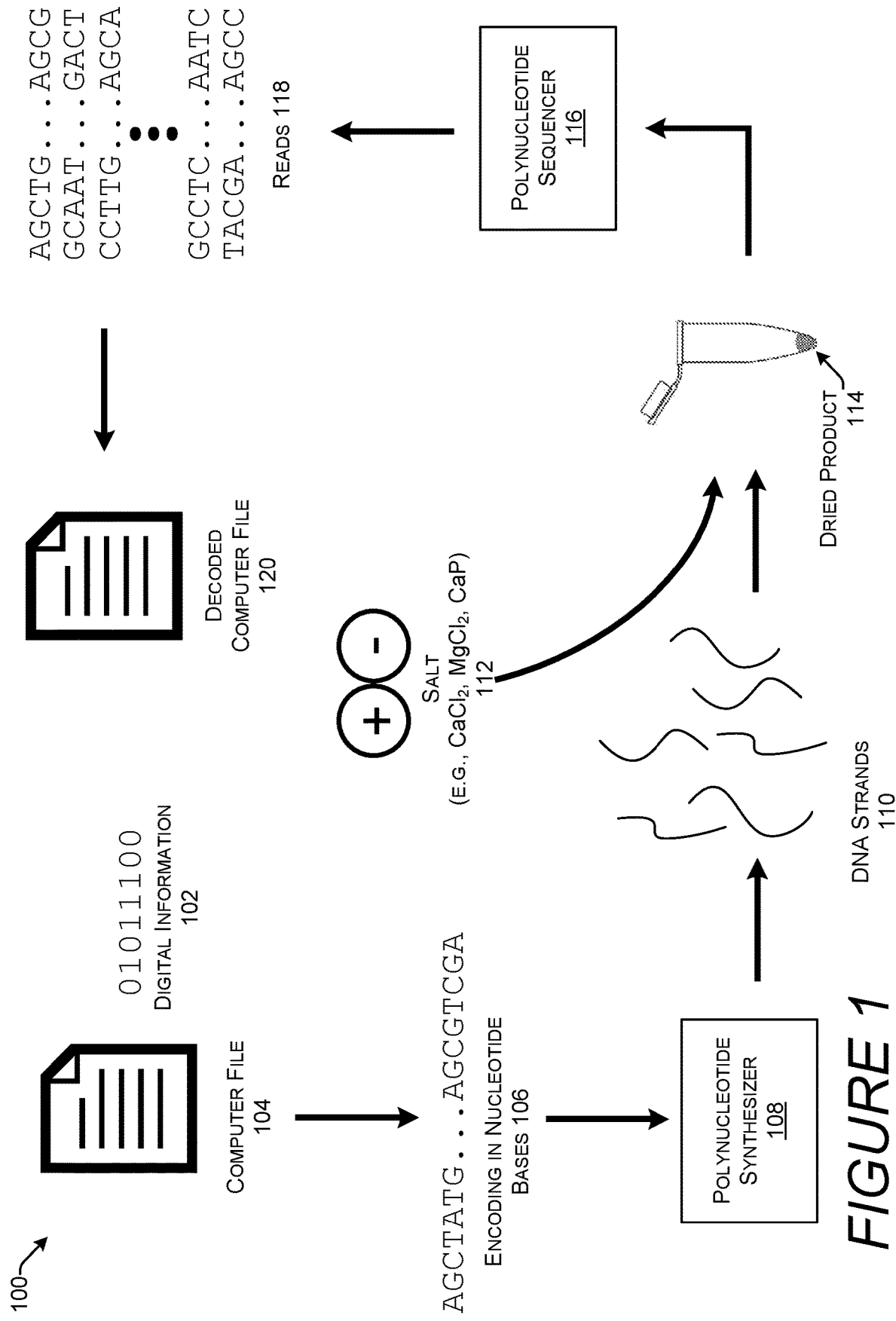
FIG. 1 is a diagram illustrating a structure and process for using a salt to stably store of DNA.

FIG. 1 illustrates a schematic representation of a process 100 for using DNA to store digital information 102 such as a computer file 104. The digital information 102 is encoded in a representation using nucleotide bases 106. Naturally occurring DNA includes four nucleotide bases: adenine (A), cytosine (C), guanine (G), and thymine (T). A DNA strand is a linear sequence of these nucleotide bases. Ribonucleic acid (RNA) has a similar structure to DNA and naturally occurring RNA has the base uracil (U) instead of thymine. Unnatural bases such as dNaM and dTPT3 may also be used. Use of unnatural bases may expand the alphabet so that there can be five, six, or more possible bases used for the encoding. Fewer than all available natural bases may be used so that the alphabet could also consist of fewer than four possible bases. "Polynucleotide" as used herein may include DNA and RNA with both natural bases and/or unnatural bases in either single stranded (ssDNA) or doubled stranded (dsDNA) structure. DNA may be used to refer to polynucleotides in general and should not be interpreted as limited to only DNA containing natural bases. An example encoding may use the bases AGC to represent the letter "a" or the bases "TG" to represent the bit "0". Thus, the digital information 102 is encoded in a string of nucleotide bases. If the encoding scheme is known, the sequence of the polynucleotide can be decoded to recover the digital information 102.

The encoding in nucleotide bases 106 represents the digital information 102 in a format that can be stored in polynucleotide molecules. Thus, this provides a way to store data in DNA. There are multiple possible techniques for encoding digital information 102, or other data, as a string of A's, G's, C's, T's, U's, and/or unnatural bases.

Once the desired sequences of the polynucleotide molecules are established, a polynucleotide synthesizer 108, creates the actual DNA strands 110. Polynucleotide synthesizers 108, also called oligonucleotide synthesizers, perform chemical synthesis of polynucleotides by joining nucleosides in a specified sequence. The specified sequence is determined by the encoding in nucleotide bases 106. With current polynucleotide synthesis technology, the chain grows in the 3' to 5' direction, which is backwards relative to natural biosynthesis. Being a chemical process, it is possible for incorrect interactions to occur leading to defective products. The longer the polynucleotide sequence that is being synthesized, the more defects there are, thus with current technology this process is only practical for producing relatively short sequences of nucleotides. The current practical limit is about 200-300 bp (base pairs) for a DNA strand 110 with sufficient quality.

The DNA strands 110 now encode the digital information 102 that was contained in a computer file 104. The DNA strands 110 may be stored until there is need to retrieve the computer file 104. The storage may be long-term storage such as archival storage in which the DNA strands 110 are kept for tens, hundreds, or even thousands of years. However, DNA may degrade and the digital information 102 lost during long-term storage unless the DNA is protected. Degraded DNA may still be present in a sample, but it can no longer be amplified by polymerase chain reaction (PCR) or sequenced. The technique described in this disclosure involves drying the DNA in the presence of a salt 112 to create a dried product 114 that contains the DNA strands 110 and the dried salt 112. The salt 112 may be, for example, calcium chloride, calcium nitrate, calcium carbonate, calcium phosphate, magnesium chloride, magnesium sulfate, magnesium nitrate, magnesium carbonate, lanthanum chloride, lanthanum nitrate, lanthanum carbonate, lanthanum bromide, or a mixture thereof.

Calcium chloride is an inorganic compound, a salt with the chemical formula $CaCl_2$. When stored dry, is a colorless crystalline solid at room temperature, highly soluble in water. Calcium chloride is commonly encountered as a hydrated solid with generic formula $CaCl_2(H_2O)x$, where x=0, 1, 2, 4, and 6. One type of calcium chloride that may be used is calcium chloride dihydrate. Calcium nitrate is an inorganic compound with the formula $Ca(NO_3)_2$. This colorless salt absorbs moisture from the air and is commonly found as a tetrahydrate. A variety of related salts are known including calcium ammonium nitrate decahydrate and calcium potassium nitrate decahydrate. Calcium carbonate is a chemical compound with the formula $CaCO_3$. The thermodynamically stable form of $CaCO_3$ under normal conditions is hexagonal $\beta$-$CaCO_3$. Calcium phosphate is a family of materials and minerals containing calcium ions ($Ca^{2+}$) together with inorganic phosphate anions. These materials contain $Ca^{2+}$ combined with $PO_4^{3-}$, $HPO_4^{2-}$, and/or $H_2PO_4^-$. Calcium phosphates are found in bone and tooth enamel of living organisms.

Magnesium chloride is the name for the chemical compound with the formula $MgCl_2$ and its various hydrates $MgCl_2(H_2O)x$. These salts are typical ionic halides, being highly soluble in water. One hydrate of magnesium chloride that may be used is magnesium dichloride hexahydrate. Magnesium sulfate is an inorganic salt with the formula $MgSO_4(H_2O)x$ where $0 \leq x \leq 7$. It is often encountered as the heptahydrate sulfate mineral epsomite ($MgSO_4.7H_2O$), commonly called Epsom salt. A variety of hydrates are known. The heptahydrate (epsomite) readily loses one equivalent of water to form the hexahydrate. The monohydrate, $MgSO_4.H_2O$ is found as the mineral kieserite. It can be prepared by heating the hexahydrate to approximately 150° C. Further heating to approximately 200° C. gives anhydrous magnesium sulfate. The heptahydrate can be prepared by neutralizing sulfuric acid with magnesium carbonate or oxide, but it is usually obtained directly from natural sources. Magnesium nitrate refers to inorganic compounds with the formula $Mg(NO_3)_2(H_2O)x$, where x=6, 2, and 0. All are white solids. The anhydrous material is hygroscopic, quickly forming the hexahydrate upon standing in air. All of the salts are very soluble in both water and ethanol. Magnesium carbonate, $MgCO_3$, is an inorganic salt that is a white solid. Several hydrated and basic forms of magnesium carbonate also exist as minerals. The most common magnesium carbonate forms are the anhydrous salt called magnesite ($MgCO_3$) and the di, tri, and pentahydrates known as barringtonite ($MgCO_3.2\ H_2O$), nesquehonite ($MgCO_3.\ 3\ H_2O$), and lansfordite ($MgCO_3.5\ H_2O$), respectively. Some basic forms such as artinite ($MgCO_3.Mg(OH)_2.3\ H_2O$), hydromagnesite (4 $MgCO_3.Mg(OH)_2.4\ H_2O$), and dypingite (4 $MgCO_3.\ Mg(OH)_2.5\ H_2O$) also occur as minerals.

Lanthanum chloride is the inorganic compound with the formula $LaCl_3$ which is also called lanthanum trichloride. It is a common salt that forms a white solid which is highly soluble in water and alcohols. Common hydrates of lanthanum chloride include the hexahydrate and the heptahydrate Lanthanum carbonate, $La_2(CO_3)_3$, is the salt formed by lanthanum(III) cations and carbonate anions. It is an ore of lanthanum metal, along with monazite. Lanthanum(III) bromide ($LaBr_3$) is an inorganic halide salt of lanthanum. When pure, it is a colorless white powder. The single crystals of $LaBr_3$ are hexagonal crystals with melting point of 783° C.

It is highly hygroscopic and water-soluble. There are also several known hydrates, $La_3Br.x\ H_2O$, of the salt.

When it is time to retrieve the digital information 102 from the DNA strands 110, the dried product 114 may be dissolved and some or all of the DNA strands 110 provided to a polynucleotide sequencer 116 to determine the sequences of the nucleotides. The polynucleotide sequencer 116 reads the order of the nucleotide bases in individual ones of the DNA strands 110. Polynucleotide sequencing includes any method or technology that is used to determine the order of the nucleotide bases—A, G, C, and T or U—in a strand of DNA or RNA. Given the convention of representing DNA nucleotides with the letters A, C, G, and T, the reads 118 generated by the polynucleotide sequencer 116 are text strings that comprise the letters A, C, G, and T. The reads 118 themselves may be in any suitable file format such as plain text, FASTQ, EMBL, or FASTA.

The reads 118 may be decoded to retrieve the digital information 102 and the binary data may be assembled to create a decoded computer file 120. Decoding of the reads 118 may be the reverse of the process used for creating the encoding in nucleotide bases 106. If the DNA strands 110 are not overly degraded during storage and any other sources of error are corrected, the decoded computer file 120 will be identical to the computer file 104. Redundancy and error-correction techniques may tolerate some level of degradation or damage to the DNA strands 110 during storage, however increasing the stability of the DNA strands 110 during storage makes long-term storage more successful and practical. If the DNA strands 110 degrade too quickly there will be no usable DNA left after many years in storage.

Illustrative Processes

For ease of understanding, the processes discussed in this disclosure are delineated as separate operations represented as independent blocks. However, these separately delineated operations should not be construed as necessarily order dependent in their performance. The order in which the process is described is not intended to be construed as a limitation, and any number of the described process blocks may be combined in any order to implement the process, or an alternate process. Moreover, it is also possible that one or more of the provided operations is modified or omitted.

Figure 2:
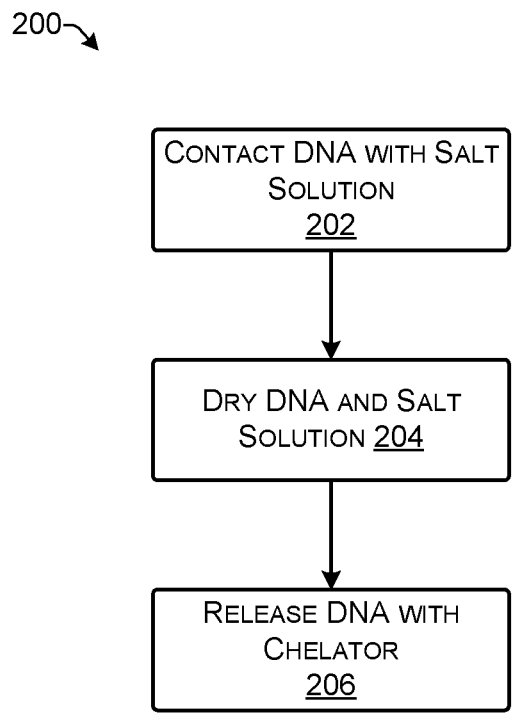
FIG. 2 is a flow diagram showing an illustrative process for storing DNA with salt.

FIG. 2 shows process 200 for using a salt solution to create a dried product that contains DNA and stably stores the DNA until separated from the salt by a chelator.

At 202, the DNA is contacted with a salt solution. The DNA may initially be in a solution of annealing buffer. The annealing buffer may be any standard buffering solution for DNA such as 400 mM Tris-HCl, 500 mM NaCl, and 100 mM $MgCl_2$. The DNA may be purified such as by removing salts from the annealing buffer. The concentration of DNA in the solution may be about 20-100 μg/ml, about 30-70 μg/ml, or about 50 μg/ml. The total amount of DNA used may be about 10-200 ng, about 20-100 ng, or about 30-50 ng. The DNA molecules may have a length of about 100-300 bp. In an implementation the length of the DNA molecules may be approximately 150 bp. The DNA may encode digital information such as all or a portion of a computer file. The salt solution may be a calcium chloride solution, magnesium chloride solution, calcium phosphate solution, lanthanum chloride solution, or mixtures thereof. The salt solution may be at a concentration of about 1 M, about 0.1 M, about 1 mM, about 0.1 mM, or about 0.01 mM. In an implementation, the salt solution may be a mixture of calcium chloride dihydrate, potassium phosphate monobasic solution, and di-potassium hydrogen orthophosphate trihydrate at a concentration of about 0.1 mM.

At 204, the DNA and salt solution are dried. Drying may be performed by any suitable technique for drying DNA in solution. In an implementation, drying may be performed by use of a centrifugal evaporator or vacuum centrifuge. A centrifugal evaporator includes a vacuum pump connected to a centrifuge chamber in which the samples are placed. The system works by lowering the pressure in the centrifuge system insert—as the pressure drops so does the boiling point of the solvent(s) in the system. When the pressure is sufficiently low that the boiling points of the solvents are below the temperature of the sample holder, then they will boil. This enables solvent to be rapidly removed while the samples themselves are not heated to damaging temperatures. The samples may be processed at room temperature or heated in the centrifugal evaporator to around 25-50° C., around 30-45° C., or around 35-40° C. Many salts are hydroscopic and adsorb moisture from the air to form hydrates after removal from the drier.

Without being bound by theory, it is believed that drying of the DNA in the presence of a suitable salt results in the DNA molecules associating with in the salt crystal in a way that stabilized the DNA. It is possible that the DNA is "encapsulated" within the crystal matrix. Support from the crystal structure and electrostatic interactions between the DNA and the salt may stabilize the DNA.

At 206, the DNA may be released from the salt by mixing with a solution of a chelator. A strong chelating agent may be used. By "strong" chelating agent it is meant that the agent binds multivalent metal ions with a comparable or better affinity than ethylene diamine tetraacetic acid (EDTA). Thus, one suitable chelator that may be used is a solution of EDTA. The chelator may be prepared at a concentration of approximately 1 mM. After release of the DNA from the salt the resulting solution may be further diluted with water or other diluent. For example, the sample may be diluted 1:100 with water. The DNA may then be sequenced with a polynucleotide sequencer or otherwise processed. The processing may include decoding the digital information stored in the sequence of the DNA.

Figure 3:
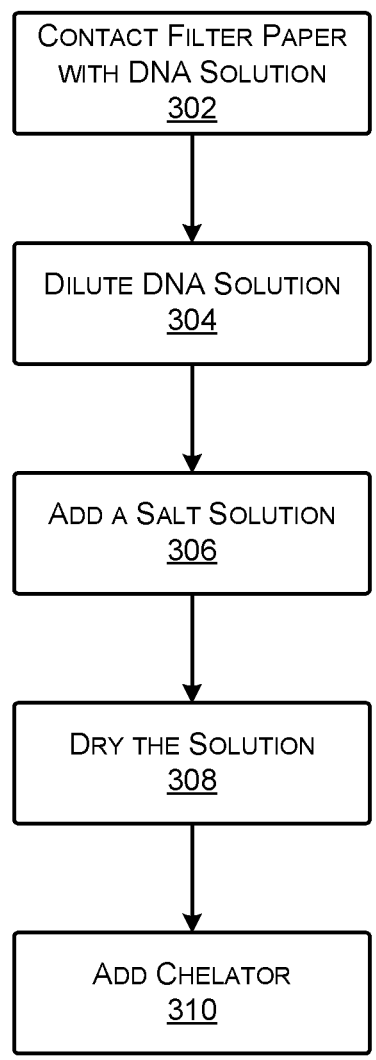
FIG. 3 is a flow diagram showing an illustrative process for storing DNA with salt.

FIG. 3 shows process 300 for using a salt solution to create a dried product that contains DNA and stably stores the DNA until separated from the salt by a chelator.

At 302, a DNA solution is placed on filter paper. The DNA may be in a solution of annealing buffer a concentration of, for example, around 40 μg/ml, 50 μg/ml, or 60 μg/ml. The annealing buffer may be any standard buffering solution for DNA. The DNA molecules in the DNA solution may have lengths of approximately 80-300 bp, approximately 100-200 bp, approximately 120-180 bp, or approximately 150 bp. The concentration of DNA in the solution may be about 20-100 μg/ml, about 30-70 μg/ml, or about 50 μg/ml. In an implementation, the DNA molecules may encode digital information such as all or a portion of a computer file.

The filter paper may be formed from biologically inert mixtures of cellulose acetate and cellulose nitrate and have a pore size of approximately 0.015-0.035 μm. In an implementation, the pore size may be 0.025 μm. Contacting the filter paper with the DNA may remove salts or other impurities from the DNA solution. An amount of the DNA solution ranging from about 10 μl to about 30 μl may be applied to a 25 mm disk of the filter paper. In an implementation, about 20 μl of the DNA solution is applied to the filter paper. The volume of DNA solution may be adjusted upwards (or downwards) if the size of the filter paper is increased (or decreased).

In an implementation, the DNA and the filter paper may be placed inside a closed container with water for about 5-30 minutes, about 15-25 minutes, or about 20 minutes. The closed container may be any type of non-reactive watertight container. One example of a suitable container is a 6-well plate. The DNA may be combined with a larger volume of water such as about 1 ml, about 2 ml, about 3 ml, or about 4 ml depending on the initial volume of DNA solution.

At 304, the DNA solution is diluted. The DNA may be diluted to a concentration of approximately 10-20 ng/µl. In an implementation, the DNA can be diluted to a concentration of approximately 15 ng/µl. The DNA concentration in the solution removed from the filter paper may be measured. Any suitable technique for measuring DNA concentration may be used. For example, the Thermo Scientific™ NanoDrop™ may be used to measure DNA concentration. Once the initial concentration is measured, a dilution ratio may be calculated.

At 306, a salt solution is added. The salt solution may supply the cation and anion for the salt that interacts with the DNA. The salt solution may be a solution of calcium chloride, magnesium chloride, calcium phosphate, lanthanum chloride, or mixtures thereof. The salt solution may be at a concentration of about 1 M, about 0.1 M, about 1 mM, about 0.1 mM, or about 0.01 mM. In an implementation, the salt solution may be magnesium dichloride hexahydrate at a concentration of about 0.1 mM.

At 308, the solution of salts and DNA is dried. The solution may be dried using any suitable technique such as a centrifugal evaporator or vacuum centrifuge. The length of time drying depends on the total volume of samples to be dried. In implementation, the drying time in a vacuum centrifuge may be 2-12 hours. The solution may be heated above room temperature to facilitate drying to, for example, heated to about 25° C., 30° C., 35° C., 40° C., or 45° C.

At 310, a chelator is added to separate the salt from the DNA. The chelator may be a strong chelating agent such as EDTA. The sample may then be diluted and analyzed by the polynucleotide sequencer or other technique.

Examples

Protocol for DNA Encapsulation in Calcium Phosphate

The following protocol describes an illustrative technique for encapsulating and de-encapsulating DNA in calcium phosphate. Techniques for other salts are similar except for the salt solutions used. After de-encapsulation of DNA from calcium phosphate, the quantity of DNA was measured by qPCR. Completing this protocol takes about 1-2 days with a total hands-on time of approximately one hour. Thus, this protocol is less labor-intensive than other DNA storage techniques such as encapsulation in silica.

Twenty µl of a DNA solution (concentration of about 50 ng/µl), such as DNA obtained from a polynucleotide synthesizer, was placed on filter paper (MF-Millipore™ Membrane Filter, 0.025 µm pore size, cat. no. VSWP02500) to remove any impurities in the DNA solution such as excess salt. The filter paper was placed inside a closed 6-well plate with ultrapure water. As used herein, "ultrapure water" refers to water having a purity such that resistivity is 18.2 MΩ·cm at 25° C. or "type 1" water as specified in ISO (International Organization for Standards) 3696. One source of ultrapure water is Milli-Q™ water available from Millipore Corporation. About 3 ml of ultrapure water were added to the container. One suitable type of 6-well plate is the Falcon™ Polystyrene Microplate (Fisher Scientific, cat. no. 08-772-49).

After 20 minutes, the maximum amount of liquid volume was removed from the filter paper. The DNA concentration in the liquid removed from the filter paper was measured. In this example, the DNA concentration was measured with a Thermo Scientific™ NanoDrop™ Other measurement technologies could be substituted for the NanoDrop™. After identifying the DNA concentration, it was diluted to a concentration of 15 ng/µl with ultrapure water.

A portion of the diluted DNA was transferred to a 2 ml Eppendorf tube. In this example, 2 µl for a total of 30 ng of DNA were transferred. Next, 5 µl of a 0.1 mM calcium chloride dihydrate solution (ACS reagent, ≥99%, CAS No. 10035-04-8, Art. no. 223506, Sigma-Aldrich) was added to the Eppendorf tube. Thereafter, 5 µl of a phosphate solution was added to the Eppendorf tube. The phosphate solution was formed from an equal volume of a 1 M potassium phosphate monobasic solution (puriss. p.a., CAS Number, 7778-77-0, Art. no. 60220, Fischer Scientific) and 1 M di-potassium hydrogen orthophosphate trihydrate solution (certified AR for analysis, CAS No. 16788-57-1, Art. No. 149926, Fisher Scientific) diluted to a final concentration of 0.1 mM potassium phosphate monobasic and 0.1 mM di-potassium hydrogen orthophosphate trihydrate. Thus, the combination has a ratio of 30 ng DNA to 0.5 nanomole (nmol) of CaP which corresponds to 1 ng DNA:16.7 picomoles (pmol) of salt. Other concentrations are also suitable such as 1 ng DNA:6-60 pmol of salt. All solutions were prepared with ultrapure water. The molar ratio of salt to DNA may range from about 20:1 to about 2:1. The molar ratio will depend on the molecular weight of the salt used and on the relative amounts of salt and DNA combined. Specifically, the molar ratio may be calculated between the cation of the salt and the negatively charged phosphate groups of the DNA.

Alternate salt solutions may be used by replacing the calcium chloride dihydrate and phosphate solutions with salt solutions at the volumes and concentrations listed below in Table 1.

TABLE 1

Concentrations, volumes, and amounts of salt solutions.

| Salt | Concentration (mM) | Volume (µl) | Amount (nmol) |
| --- | --- | --- | --- |
| Calcium chloride dihydrate | 0.1 | 5 | 0.5 |
| Magnesium dichloride hexahydrate | 0.1 | 5 | 0.5 |
| Lanthanum trichloride | 0.01 | 20 | 0.2 |
| Barium (II) chloride dihydrate | 0.1 | 5 | 0.5 |
| Strontium chloride hexahydrate | 0.01 | 20 | 0.2 |
| Sodium chloride | 0.1 | 20 | 2.0 |
| Copper (II) chloride anhydrous | 0.1 | 5 | 0.5 |

The mixture of solutions in the Eppendorf tube was placed in a vacuum centrifuge (Eppendorf Concentrator plus or Vacufuge plus) to remove the water. The sample was dried in the vacuum centrifuge at about 30-45° C. for two hours. Total drying time may be between about 2-12 hours depending on the number of samples and capacity of the vacuum centrifuge. This created a dried product that contained the DNA and calcium phosphate. Without being bound by theory, it is believed that the DNA may have been encapsulated in the calcium phosphate. DNA loading data presented below was generated from analysis of dried products created with this technique. At this point, the compositions containing DNA may be stored potentially for many years, decades, or longer.

The DNA was separated from the salt by mixing with 100 µl of 1 mM EDTA. The Eppendorf tube was briefly vortexed after addition of the EDTA. The sample was then diluted 1:100 with ultrapure water. Further dilution was performed by taking 5 µl of the diluted sample and adding that to 495 µl of ultrapure water. This 500 µl volume is suitable for sequencing or analysis by qPCR.

Loading and Stability Tests

Table 2 below shows a comparison of DNA loading and stability in various salts. The compositions of DNA and the various salts were prepared according to the protocol described above. Untreated DNA was prepared using a similar protocol and dried without the presence of a salt. The DNA samples were stored in an oven at at 70° C. and 50% RH for a week to simulate approximately 2000 years of storage at room temperature. Thus, one day of storage at 70° C. is believed to simulate as many as 286 years of storage at room temperature.

DNA loading was measured as the percent of the dried product by weight that is DNA out of the total weight (wt %). Specifically, the DNA wt % was calculated by dividing the weight of DNA (i.e., calculated from a concentration and volume of DNA solution) by the total weight of the DNA and the salt (i.e., calculated from a known volume of salt solution at a known molarity). For example, if 30 ng of DNA is dried together with 100 ng of $CaCl_2$ then the dry wt % of DNA is 30±(30+100)=23. The weight percent of DNA will decrease for hydrated salts that have absorbed moisture from the environment.

DNA stability was measured by comparing the starting amount of DNA present in the samples to the amount present after storage at 70° C. for a week. Quantitative PCR (qPCR) was used to measure the amount of DNA in a sample. qPCR uses the linearity of DNA amplification to determine the quantity of DNA in a sample. By using a fluorescent reporter in the reaction, it is possible to measure DNA generation in the qPCR assay as the PCR reaction proceeds in real time. The number of PCR cycles at which the fluorescence exceeds a detection threshold and becomes measurable is called the quantification cycle (Cq). Starting samples that include a larger amount of DNA reach this threshold with fewer PCR cycles than samples with a smaller amount of DNA. For sequences with an optimal PCR efficiency (100%), each PCR cycle doubles the quantity of DNA, so an increase in Cq value of 1 is equivalent to detecting a 50% loss of the initial quantity of DNA. Thus, Cq values are inversely proportional to the amount of target DNA in the sample.

The change in number of PCR cycles to Cq for a sample after storage at 70° C. is ΔCq. If the difference was zero, that would indicate no loss of DNA. A value of two indicates that only 25% of the original quantity of DNA remained. Daily ΔCq values were calculated by dividing the total change in Cq during a week by seven. The error of ΔCq/day values is ±5%.

TABLE 2

DNA loadings and DNA stability in various salts compared to untreated DNA.

| Salt | DNA Loading (wt %) | DNA Stability (ΔCq/day) |
| --- | --- | --- |
| $CaCl_2$ | 35 | 0.86 |
| $MgCl_2$ | 39 | 0.85 |
| CaP | 18 | 1.09 |
| $LaCl_3$ | 38 | 1.01 |
| $BaCl_2$ | 22 | 2.62 |
| $SrCl_2$ | 36 | 1.66 |
| NaCl | 20 | 2.13 |
| $CuCl_2$ | 31 | 2.63 |
| Untreated DNA | 100 | 2.64 |

The DNA wt % of the dried products ranged from 18 to 39. Calcium phosphate held the least DNA (18 wt %) while magnesium chloride and lanthanum chloride held the most (38 and 39 wt %).

Untreated DNA dried without the presence of a salt loses 2-3 PCR cycles per day at 70° C. and 50% RH. The greatest stability was achieved by use of calcium chloride and magnesium chloride which reduced the rate of DNA degradation to less than one PCR cycle per day (i.e., <50% loss). This represents more than a threefold improvement in stability as compared to untreated DNA. If stored at room temperature, use of calcium chloride or magnesium chloride would preserve approximately 59% of the DNA after 286 years. When stored with calcium phosphate, approximately 1.1 PCR cycles were lost per day which corresponds with more than approximately 45% of the DNA remaining in the composition. Use of strontium chloride or sodium chloride provided only small improvements in stability. Drying DNA in the presence of barium chloride or copper chloride did not improve stability.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A method comprising: diluting a solution containing DNA; adding a salt solution at a molar ratio of less than 20:1 salt cation to phosphate groups in the DNA; and drying to create a dried product.

Clause 2. The method of clause 1, wherein the DNA comprises strands of dsDNA about 100-200 bp long.

Clause 3. The method of any of clauses 1-2, wherein a cation in the salt solution is calcium, magnesium, or lanthanum.

Clause 4. The method of clause 3, wherein the molar ratio is less than 10:1.

Clause 5. The method of any of clauses 1-4, wherein drying comprises drying in a vacuum centrifuge for at least two hours.

Clause 6. The method of any of clauses 1-5, wherein ratio of DNA to salt is about 1 ng:6-60 pmol.

Clause 7. The method of any of clauses 1-6, wherein the dried product comprises at least 10% DNA by weight and less than about half of the DNA degrades during storage at about 70° C. for 24 hours.

Clause 8. The method of any of clauses 1-7, further comprising contacting a filter paper with the solution containing DNA prior to the diluting.

Clause 9. The method of any of clauses 1-8, further comprising adding a strong chelator to the dried product to release the DNA.

Clause 10. A method of stabilizing DNA comprising: contacting the DNA with a salt solution; and drying the DNA and salt solution to create a dried product, wherein the dried product has at least 5% DNA by weight.

Clause 11. The method of clause 10, wherein a cation of the salt solution is calcium, magnesium, or lanthanum.

Clause 12. The method of any of clauses 10-11, wherein the drying comprises drying with a vacuum centrifuge.

Clause 13. The method of any of clauses 10-12, wherein the dried product has at least 15% DNA by weight.

Clause 14. The method of any of clauses 10-13, wherein after 24 hours at 70° C. more than 45% of the DNA in the precipitate remains.

Clause 15. The method of any of clauses 10-14, further comprising placing the DNA on filter paper prior to contacting the DNA with the salt solution.

Clause 16. The method of any of clauses 10-15, further comprising releasing the DNA from the dried product by contacting the dried product with a chelator.

Clause 17. A composition of matter comprising a mixture that includes at least 20% DNA by weight and a salt, wherein the DNA is heat stable.

Clause 18. The composition of matter of clause 17, wherein a cation of the salt is calcium, magnesium, or lanthanum.

Clause 19. The composition of matter of any of clauses 17-18, wherein the mixture includes at least 35% DNA by weight.

Clause 20. The composition of matter of any of clauses 17-19, wherein the DNA in the mixture is heat stable at 70° C. and 50% relative humidity such that less than 50% of the DNA degrades per 24-hour period.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention (especially in the context of the following claims) are to be construed to cover both the singular and the plural, unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications (collectively "references") throughout this specification. Each of the cited references is individually incorporated herein by reference for its particular cited teachings as well as for all that they disclose.

The invention claimed is:

1. A method comprising:
    diluting a solution containing DNA;
    adding a salt solution at a molar ratio of less than 20:1 salt cation to phosphate groups in the DNA; and
    drying to create a dried product, wherein the dried product does not include a solid phase media.

2. The method of claim 1, wherein the DNA comprises strands of dsDNA about 100-200 bp long.

3. The method of claim 1, wherein a cation in the salt solution is calcium, magnesium, or lanthanum.

4. The method of claim 3, wherein the molar ratio is less than 10:1.

5. The method of claim 1, wherein drying comprises drying in a vacuum centrifuge for at least two hours.

6. The method of claim 1, wherein the molar ratio of DNA to salt is about 1 ng:6-60 pmol.

7. The method of claim 1, further comprising contacting a filter paper with the solution containing DNA prior to the diluting.

8. The method of claim 1, further comprising adding a strong chelator to the dried product to release the DNA.

9. A method of stabilizing DNA comprising:
    calculating a weight of the DNA;
    selecting a weight of a salt solution such that a dried product has at least 5% DNA by weight;
    contacting the DNA with the salt solution; and
    drying the DNA and salt solution to create the dried product, wherein the dried product does not include a solid phase media.

10. The method of claim 9, wherein a cation of the salt solution is calcium, magnesium, or lanthanum.

11. The method of claim 9, wherein the drying comprises drying with a vacuum centrifuge.

12. The method of claim 9, wherein the weight of the salt solution is selected such that the dried product has at least 15% DNA by weight.

13. The method of claim 9, further comprising placing the DNA on filter paper prior to contacting the DNA with the salt solution.

14. The method of claim 9, further comprising releasing the DNA from the dried product by contacting the dried product with a chelator.

15. A composition of matter comprising a mixture that includes at least 20% DNA by weight and a salt, wherein the DNA is heat stable and the composition of matter does not include a solid phase media.

16. The composition of matter of claim 15, wherein a cation of the salt is calcium, magnesium, or lanthanum.

17. The composition of matter of claim 15, wherein the mixture includes at least 35% DNA by weight.

18. The composition of matter of claim 15, wherein the DNA in the mixture is heat stable at 70° C. and 50% relative humidity such that less than 50% of the DNA degrades per 24-hour period.

19. The method of claim 1, wherein the salt solution is calcium chloride or magnesium chloride and wherein the molar ratio of less than 20:1 salt cation to phosphate groups in the DNA is selected such that the dried product has at least 30% DNA by weight.

20. The method of claim 9, wherein the salt solution is calcium chloride or magnesium chloride and wherein the weight of the salt solution is selected such that the dried product has at least 30% DNA by weight.

\* \* \* \* \*